United States Patent
Hill et al.

(10) Patent No.: US 12,246,038 B2
(45) Date of Patent: Mar. 11, 2025

(54) COMPOSITIONS FOR INDUCING AN IMMUNE RESPONSE

(71) Applicant: OXFORD UNIVERSITY INNOVATION LIMITED, Oxford (GB)

(72) Inventors: Adrian V S Hill, Oxford (GB); Irina Redchenko, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 1114 days.

(21) Appl. No.: 17/055,056

(22) PCT Filed: May 16, 2019

(86) PCT No.: PCT/EP2019/062694
§ 371 (c)(1),
(2) Date: Nov. 12, 2020

(87) PCT Pub. No.: WO2019/219851
PCT Pub. Date: Nov. 21, 2019

(65) Prior Publication Data
US 2021/0213060 A1    Jul. 15, 2021

(30) Foreign Application Priority Data
May 16, 2018   (GB) ..................................... 1807932

(51) Int. Cl.
| A61K 35/17 | (2015.01) |
| A61K 39/00 | (2006.01) |
| C07K 16/28 | (2006.01) |
| C12N 15/86 | (2006.01) |

(52) U.S. Cl.
CPC ........ *A61K 35/17* (2013.01); *A61K 39/00118* (2018.08); *A61K 39/001193* (2018.08); *C07K 16/2818* (2013.01); *C12N 15/86* (2013.01); C12N 2710/24143 (2013.01)

(58) Field of Classification Search
None
See application file for complete search history.

(56) References Cited

U.S. PATENT DOCUMENTS

2005/0123918 A1* 6/2005 Carroll ..................... A61P 37/04
                                                     435/372
2013/0195912 A1* 8/2013 Cottingham ........... A61K 48/00
                                                     435/320.1

FOREIGN PATENT DOCUMENTS

| WO | 2011/128704 A1 | 10/2011 |
| WO | 2011128704 | 10/2011 |
| WO | 2014063832 | 5/2014 |

OTHER PUBLICATIONS

Genbank Accession No. Z29083, earliest publication date 1994, 2 pages.*
Notice of Reason for Refusal for Japanese Patent Application No. 2020-561892, mailed Apr. 17, 2023, 11 Pages including English Translation.
Amato et al., "Vaccination of Prostate Cancer Patients With Modified Vaccinia Ankara Delivering the Tumor Antigen 5T4 (TroVax) A Phase 2 Trial", J Immunother, vol. 31, Issue 6, Jul.-Aug. 2008, pp. 577-585.
Alharbi et al., "Enhancing cellular immunogenicity of MVA-vectored vaccines by utilizing the F11 L endogenous promoter", Vaccine, 2016, vol. 34, pp. 49-55.
Cappuccini et al., "Immunogenicity and efficacy of the novel cancer vaccine based on simian adenovirus and MVA vectors alone and in combination with PD-1 mAb in a mouse model of prostate cancer", Cancer Immunol Immunother, 2016, vol. 65, pp. 701-713.
Harrop et al., "Vaccination of Colorectal Cancer Patients with Modified Vaccinia Ankara Delivering the Tumor Antigen 5T4 (TroVax) Induces Immune Responses which Correlate with Disease Control: A Phase I/II Trial", Clin Cancer Res., Jun. 1, 2006, vol. 12, Issue 11, pp. 3416-3424.
Request for The Submission of an Opinion, for Korean Patent Application No. 10-2020-7036057, mailed Aug. 31, 2023, 14 Pages including English Translation.
Cappuccini et al., "5T4 oncofoetal glycoprotein: an old target for a novel prostate cancer immunotherapy", Oncotarget, 2017, vol. 8, Issue 29, pp. 47474-47489.
International Search Report and Written Opinion received for International Patent Application No. PCT/EP2019/062694, mailed on Sep. 19, 2019, 11 pages.
International Preliminary Report on Patentability received for International Patent Application No. PCT/US2018/046318, mailed on Nov. 26, 2020, 8 pages.
Siegel et al., "Cancer statistics 2014", Cancer Journal for Clinicians, vol. 64, Issue 1, Jan. 7, 2014, pp. 9-29.
Challis et al., "The Spontaneous Regression of Cancer: A review of cases from 1900 to 1987", Acta Oneal., vol. 29, 1990, pp. 545-550.
Zhang et al., "Intratumoral T Cells, Recurrence, and Survival in Epithelial Ovarian Cancer", N Engl J Med., vol. 348, 2003, pp. 203-213.
Ewer et al., "Protective CD8ρ T-cell immunity to human malaria induced by chimpanzee adenovirus—MVA immunisation", Nat Commun., vol. 4, Issue 3836, 2013, 10 Pages.
Antrobus et al. "Clinical Assessment of a Novel Recombinanat Simian Adenovirus ChAdOx1 as a Vectored Vaccine Expressing Conserved Influenza A Antigens", J Am Soc Gene Therapy, vol. 22, 2024, pp. 668-674.

(Continued)

*Primary Examiner* — Christopher M Babic
*Assistant Examiner* — Kimberly A Aron
(74) *Attorney, Agent, or Firm* — Nicholas J. Landau; Maynard Nexsen PC

(57) ABSTRACT

The invention relates to a composition for inducing a T cell mediated immune response for the treatment or prevention of prostate cancer comprising a modified Vaccinia virus Ankara (MVA) vector expressing the 5T4 antigen polypeptide under control of a poxvirus F11 promoter. Suitably said poxvirus F11 promoter is the endogenous MVA F11 promoter. More suitably said vector expresses a polypeptide having the amino acid sequence of SEQ ID NO: 1 or said vector expresses a polypeptide encoded by a polynucleotide having the nucleic acid sequence of SEQ. ID NO: 2. The invention also relates to uses and methods.

4 Claims, 4 Drawing Sheets
Specification includes a Sequence Listing.

(56) References Cited

OTHER PUBLICATIONS

Borthwick et al., "Vaccine-elicited Human T Cells Recognizing Conserved Protein Regions Inhibit HIV-1", Mol Ther. vol. 22, 2014, pp. 464-475.
Swadling et al., "A human vaccine strategy based on chimpanzee adenoviral and MVA vectors that primes, boosts, and sustains functional HCV-specific T cell memory", Science translational medicine, vol. 6, Issue 261, Nov. 5, 2014, 32 Pages.
Hodgson et al., "Evaluation of the Efficacy of ChAd63-MVA Vectored Vaccines Expressing Circumsporozoite Protein and ME-TRAP Against Controlled Human Malaria Infection in Malaria-Naive Individuals",. J Inf Dis., vol. 211, Issue 7, Apr. 1, 2015, pp. 1076-1086.
Ewer et al., "A Monovalent Chimpanzee Adenovirus Ebola Vaccine Boosted with MVA", New Engl J Med., vol. 374, Issue 17, Apr. 28, 2016, pp. 1635-1646.
Southall et al., "Immunohistological distribution of 5T4 antigen in normal and malignant tissues", Br J Cancer, vol. 61, 1990, pp. 89-95.
Starzynska et al., "Prognostic significance of 5T4 oncofetal antigen expression in colorectal carcinoma", Br J Cancer, vol. 69, 1994, pp. 899-902.
Amato et al., "Evaluation of MVA-5T4 as a novel immunotherapeutic vaccine in colorectal, renal and prostate cancer"; Future Oncol., vol. 8, Issue 3, 2012, pp. 231-237.
Stern et al., "Understanding and exploiting 5T4 oncofoetal glycoprotein expression", Seminars in Cancer Biology. vol. 29, 2013, pp. 13-20.
Stern et al., "5T4 oncofoetal antigen: an attractive target for immune intervention in cancer", Cancer Immunology, Immunotherapy. vol. 66, 2016:pp. 415-426.
Kim et al., "TroVax, a recombinant modified vaccinia Ankara virus encoding 5T4: Lessons learned and future development", Human Vaccines. vol. 6, Issue 10, pp. 784-791.
Al-Taei et al., "Overexpression and potential targeting of the oncofoetal antigen 5T4 in malignant pleural mesothelioma", Lung Cancer, vol. 77, Issue 2, Aug. 2012, pp. 312-318.
Harrop et al., "Analysis of pre-treatment markers predictive of treatment benefit for the therapeutic cancer vaccine MVA-5T4 (TroVax)" Cancer Immunology, Immunotherapy. vol. 61, 2012, pp. 2283-2294.
Redchenko et al., "VANCE: first in human phase I study of a novel ChAdOx1-MVA 5T4 vaccine in low and intermediate risk prostate cancer", webpage available at https://ora.ox.ac.uk/objects/uuid:d811b39f-a8f4-4fb4-a5b7-b513a90fdc25/files/m0e1582e47642e48f7dc7e0f621075a95.
Harrop et al., "Vaccination of castration-resistant prostate cancer patients with TroVax (MVA-5T4) in combination with docetaxel: a randomized phase II trial" Cancer Immunology, Immunotherapy. 2013.
Sitch, David, "International Search Report and Written Opinion for PCT/EP2019/062694," European Patent Office Searching Authority, Sep. 19, 2019.
Harrop, Richard, et al., "Vaccination of castration-resistant prostate cancer patients with TroVaz (MVA-5T4) in combination with docetaxel: a randomized phase II trial," Cancer Immunol Immunother, vol. 62, No. 9., Jul. 23, 2013.
Orubu, Toritse, et al., "Expression and Cellular Immunogenicity of a Transgenic Antigen Driven by Endogenous Poxviral Early Promoters at Their Authentic Loci in MVA", PLOS ONE, vol. 7, No. 6, Jun. 27, 2012.

* cited by examiner

Figure 1

SEQ ID NO:1

MPGGCSRGPAAGDGRLRLARLALVLLGWVSSSSPTSSASSFSSSAPFLASAVS
AQPPLPDQCPALCECSEAARTVKCVNRNLTEVPTDLPAYVRNLFLTGNQLAVL
PAGAFARRPPLAELAALNLSGSRLDEVRAGAFEHLPSLRQLDLSHNPLADLSP
FAFSGSNASVSAPSPLVELILNHIVPPEDERQNRSFEGMVVAALLAGRALQGL
RRLELASNHFLYLPRDVLAQLPSLRHLDLSNNSLVSLTYVSFRNLTHLESLHL
EDNALKVLHNGTLAELQGLPHIRVFLDNNPWVCDCHMADMVTWLKETEVVQGK
DRLTCAYPEKMRNRVLLELNSADLDCDPILPPSLQTSYVFLGIVLALIGAIFL
LVLYLNRKGIKKWMHNIRDACRDHMEGYHYRYEINADPRLTNLSSNSDV

Figure 2

SEQ ID NO:2

ATGCCTGGCGGCTGTAGCAGAGGACCTGCTGCTGGCGACGGTAGACTGAGACT
GGCTAGACTGGCACTGGTGCTGCTTGGCTGGGTGTCCTCTAGCAGCCCTACAA
GCAGCGCCAGCTCCTTTAGCAGCAGCGCCCCTTTTCTGGCCTCTGCCGTTTCT
GCTCAACCTCCTCTGCCTGATCAGTGCCCTGCTCTGTGCGAGTGTTCTGAGGC
CGCCAGAACAGTGAAGTGCGTGAACAGAAACCTGACCGAGGTGCCCACAGACC
TGCCTGCCTACGTGCGGAATCTGTTCCTGACCGGAAATCAGCTGGCCGTGCTT
CCTGCTGGCGCCTTTGCTAGAAGGCCTCCACTGGCTGAACTGGCCGCTCTGAA
TCTGAGCGGCAGCAGACTGGATGAAGTTCGCGCTGGCGCTTTCGAGCATCTGC
CTTCTCTGAGACAGCTGGACCTGAGCCACAATCCTCTGGCCGATCTGAGCCCC
TTTGCCTTCAGCGGAAGCAACGCCTCTGTGTCTGCTCCATCTCCACTGGTCGA
GCTGATCCTGAACCACATCGTGCCTCCAGAGGACGAGCGGCAGAACAGATCCT
TTGAAGGCATGGTGGTGGCTGCCCTGCTTGCTGGTAGAGCACTGCAAGGACTG
CGGAGACTGGAACTGGCCAGCAACCACTTCCTGTACCTGCCTAGAGATGTGCT
GGCCCAGCTGCCTAGCCTGAGGCATCTGGATCTGTCCAACAACAGCCTGGTGT
CCCTGACCTACGTGTCCTTCCGGAATCTGACCCACCTGGAAAGCCTGCACCTG
GAAGATAACGCCCTGAAGGTGCTGCACAATGGCACCCTGGCAGAACTGCAGGG
CCTGCCTCACATCAGAGTGTTTCTGGACAACAACCCCTGGGTCTGCGACTGCC
ACATGGCCGATATGGTCACCTGGCTGAAAGAAACCGAGGTGGTGCAGGGCAAA
GACCGGCTGACATGTGCTTACCCCGAGAAGATGCGGAACCGGGTGCTGCTGGA
ACTGAACAGCGCCGACCTGGACTGCGATCCTATTCTGCCACCTAGCCTGCAGA
CCAGCTACGTGTTCCTGGGAATCGTGCTGGCTCTGATCGGCGCCATCTTTCTG
CTGGTGCTGTACCTGAACCGGAAGGGCATCAAGAAATGGATGCACAACATCCG
GGACGCCTGCCGGGATCACATGGAAGGCTACCACTACAGATACGAGATCAACG
CCGATCCTCGGCTGACCAACCTGAGCAGCAATAGCGACGTGTGATGA

Figure 3
A     Ex vivo IFNγ ELISPOT, blood
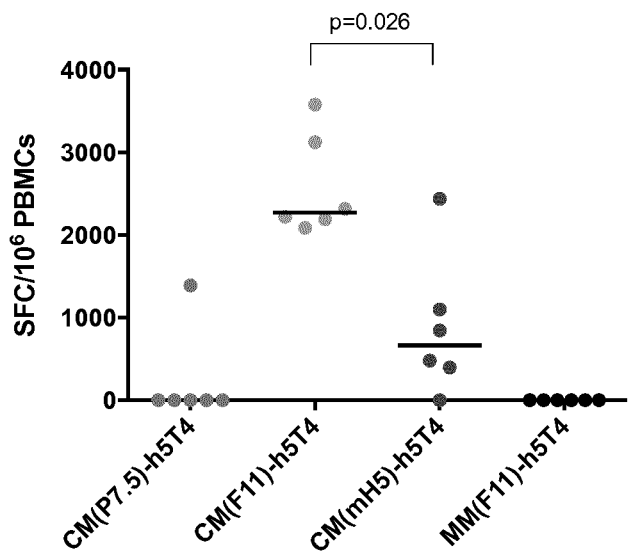
B     Ex vivo IFNγ ELISPOT, spleen
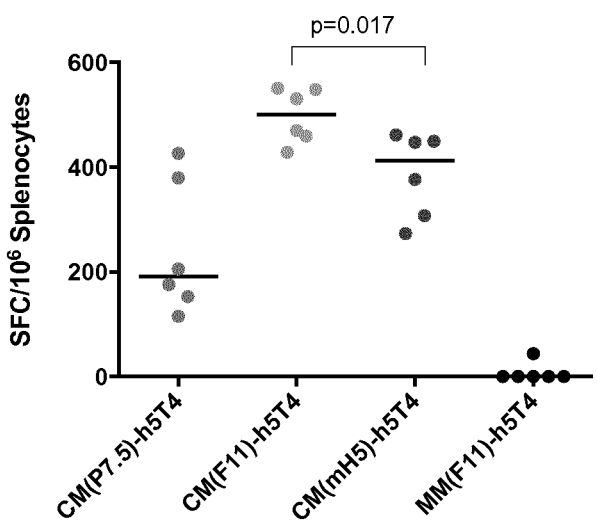

COMPOSITIONS FOR INDUCING AN IMMUNE RESPONSE

CROSS-REFERENCE TO RELATED APPLICATIONS

This application is a national stage under 35 U.S.C. 371 of International Application No. PCT/EP2019/062694 having an international filing date of May 16, 2019 (currently published). International Application No. PCT/EP2019/062694 cites the priority of GB Patent Application No. 1807932.7, filed May 16, 2018 (abandoned).

FIELD OF THE INVENTION

The invention relates to induction of immune responses, suitably protective immune responses, against tumour antigens associated with prostate cancer.

BACKGROUND TO THE INVENTION

Prostate cancer is the most common non-skin cancer and the second leading cause of cancer deaths in men. Approximately 1.1 million men were diagnosed with this disease globally in 2012 thus accounting for 15% of all cancer diagnoses in men. More than 70% of cases of prostate cancer occur in the developed world. For example, in the USA alone in 2014 an estimated 233,000 men were diagnosed with this disease and approximately 30,000 deaths were predicted (Siegel et al (2014). CA Cancer J Clin 64:9-29). While there have been significant advances in prostate cancer treatment, there are few treatments available for advanced stages of the disease and these have demonstrated unsatisfactory effectiveness. Therefore, development of effective therapies remains a high priority for treatment of this disease.

Efforts have intensified to develop active immunotherapies (vaccines) for cancer including prostate cancer. Traditional vaccines have been effective in the induction of protective immunity to pathogens based on recognition of foreign, "non-self" antigens. However, the vast majority of cancer antigens characterized to date are unaltered "self" antigens that are expressed by tumor and normal cells. This poses a challenge in the development of effective active immunotherapies for cancer. Despite this limitation on immune surveillance and clearing of cancer, cancer immunity has been observed clinically in the form of various tumours (Challis & Stam (1990). Acta Oncol. 29:545-550). In addition, histopathology of tumor sections has revealed infiltrating lymphocytes around the tumor bed, and recent studies indicate that ovarian cancer patients with such infiltrates around the tumors have an improved prognosis, compared with similarly staged patients without lymphocytic infiltrates (Zhang et al (2003). N Engl J Med. 348:203-213). The immune repertoire therefore contains auto-reactive immune cells that may reject tumors, when activated appropriately. These auto-reactive cells, upon recognizing target molecules on normal cells, also have the potential to induce tissue destruction leading to toxic autoimmunity. Accordingly, development of therapies aimed at activating host anti-tumour immunity using appropriate immunological targets remains a promising route to success in treating cancers including prostate cancer.

T cells are known to be important in immune control of cancer, and a significant body of evidence accumulated over the last two decades has shown that prime-boost protocols involving sequential administration of different vectors encoding the same antigen(s) yield considerably higher immune responses with protective capability in several animal models and clinical trials. In fact, a vaccination strategy based on the simian adenovirus prime and MVA boost proved to be the most powerful approach for the induction of polyfunctional protective T cell responses against some human pathogens in clinical trials (Ewer et al (2013). Nat Commun. 4:2836; Antrobus et al (2014). J Am Soc Gene Therapy. 22:668-674; Borthwick et al. (2014). Mol Ther. 22:464-475; Swadling et al (2014). Science translational medicine. 6:261ra153; Hodgson et al (2015). J Inf Dis. 211:1076-1086; and Ewer et al (2016). New Engl J Med. 374:1635-1646).

Although promising, the use of therapeutic vaccination in cancer presents many challenges, with tolerance to self-antigens and active immunosuppressive mechanisms mounted by tumours being two major factors hampering efficacy. The two most advanced prostate cancer immunotherapies, Sipuleucel-T and ProstVac, target two well-defined prostate cancer antigens, prostatic acid phosphatase (PAP) and prostate-specific antigen (PSA), respectively. 5T4, an oncofoetal glycoprotein that belongs to the family of shared tumour antigens, is another promising antigen candidate for a prostate cancer vaccine. It was identified in 1990 by searching for shared surface molecules of human trophoblast and cancer cells, with the rationale that they may have a function in survival of the foetus as a semi-allograft (Southall et al (1990). Br J Cancer. 61:89-95). 5T4 has been a subject of intensive exploration as a potential target for cancer immunotherapy because of its high expression in a wide range of human solid malignancies (Southall et al. (1990). Br J Cancer. 61:89-95; Starzynska et al (1994). Br J Cancer. 69:899-902; and Amato & Stepankiw (2012). Future Oncol. 8:231-237) and an apparent correlation of its expression with disease progression (Stern et al (2014). Seminars in Cancer Biology. 29:13-20; and Stern & Harrop (2016). Cancer Immunology, Immunotherapy. 2016:1-12).

Clinical testing of the 5T4-targeting vaccine started more than a decade ago, with the 5T4 protein expressed from the modified vaccinia Ankara virus (MVA). This vaccine was administered to late stage colorectal cancer patients as a homologous prime-boost vaccine known under the trade name of TroVax, and it has been given to over 500 patients with colorectal, breast, renal, prostate cancer and mesothelioma to date in the course of phase I-III clinical trials (Kim et al (2010). Human Vaccines. 6:784-791; and Al-Taei et al (2012). Lung Cancer. 77:312-318). TroVax had a good safety profile and was well tolerated with a trend toward improved progression-free survival in those patients with the highest 5T4-specific antibody titres (Harrop et al (2010); however, vaccine-specific cellular immune responses and clinical efficacy were modest, J immunotherapy. 33:999-1005; and Harrop et al (2012). Cancer Immunology, Immunotherapy. 61:2283-2294).

Harrop et al (Cancer Immunology, Immunotherapy 2014, 62(9); 1511-1520) disclosed the results of clinical administration of TroVax®, a MVA expressing the 5T4 antigen under control of the mH5 (modified H5) early promoter, with docetaxel in castration-resistant prostate cancer patients. The study demonstrated vaccine tolerance in all patients and greater median progression-free survival for patients receiving TroVax® plus docetaxel compared to those receiving docetaxel alone. However, the measured increase in treatment efficacy was modest.

Cappuccini et al (Oncotarget 2017, 8(29); 47474-47489) compared administration of MVA expressing unmodified 5T4 antigen and the same antigen fused to the MHC class 2-associated invariant chain (Ii) under the control of the p7.5 late promoter as part of a heterologous prime-boost regimen in a mouse model of prostate cancer. This study demonstrated an antibody response to unmodified 5T4, but no measurable T cell response was reported except for the modified antigen. This lack of a T cell immune response to the unmodified "self" antigen indicates that MVA expressing unmodified 5T4 under the control of the p7.5 promoter is unlikely to be an effective anti-tumour vaccine.

Thus, there is no vaccine in the prior art that is demonstrated to deliver effective treatment or protection against prostate cancer either alone or in combination with any other therapeutic agents.

The present seeks to overcome problem(s) associated with the prior art.

SUMMARY OF THE INVENTION

We describe a combination which comprises a modified Vaccinia virus Ankara (MVA) vector expressing the 5T4 protein antigen under the control of the endogenous viral F11 promoter. The present invention is based on the surprising finding by the inventors that expression of 5T4 from the endogenous F11 promoter of MVA was sufficient to break tolerance and induce 5T4-specific T cell immune responses when used as part of a prime-boost regimen following initial immunisation with an adenoviral construct expressing 5T4. Compositions of the invention are therefore useful in breaking tolerance to induce antigen-specific immune responses to treat prostate cancer. Data demonstrating these advantages are provided in the figures and examples below.

In a first aspect, the invention provides composition for inducing a T cell mediated immune response for the treatment or prevention of prostate cancer comprising a modified Vaccinia virus Ankara (MVA) vector expressing the 5T4 antigen polypeptide under control of a poxvirus F11 promoter.

The compositions of the first aspect can be advantageously used to break immune tolerance to and induce T cell-mediated immune responses against the 5T4 antigen, and this can allow effective treatment or prevention of prostate cancer.

The 5T4 polypeptide expressed by the composition of the first aspect can have the amino acid sequence of SEQ ID NO:1 or it can have an amino acid sequence encoded by the nucleic acid sequence of SEQ ID NO:2.

Advantageously, the composition may further comprise an adjuvant, and the composition may be used for inducing a T cell mediated immune response against the 5T4 antigen polypeptide in a subject and for the treatment or prevention of prostate cancer.

BRIEF DESCRIPTION OF THE DRAWINGS

The present invention will now be described by way of example, with reference to the accompanying drawings, in which:

FIG. 1 shows the amino acid sequence of 5T4 antigen (SEQ ID NO:1).

FIG. 2 shows the nucleic acid sequence encoding the full-length 5T4 antigen (SEQ ID NO: 2).

FIG. 3 illustrates the magnitude of 5T4-specific T cell responses in blood is significantly higher following the boost with MVA.5T4 expressing 5T4 under the control of F11 promoter compared to the mH5 promoter driven expression. C57BL/6 mice were immunised intramuscularly at three week intervals with $10^{10}$ VP of ChAdOx1 vectors expressing the h5T4 antigen followed by $10^7$ pfu of MVA vectors expressing the h5T4 under control of p7.5, F11, and mH5 promoters or were given a homologous MVA.h5T4 prime-boost at $10^7$ pfu with the antigen expression driven by F11 promoter. Graphs show representative data of ex vivo blood (A) and spleen (B) ELISPOT performed after prime-boost immunisations. X axis: dosing regimens for groups 1-4. Y axis: number of spot forming cells (SFC) per $10^6$ PBMCs. Bars represent median. (C=ChAdOx1, M=MVA). Significant p values are shown.

DETAILED DESCRIPTION

Figure 4:
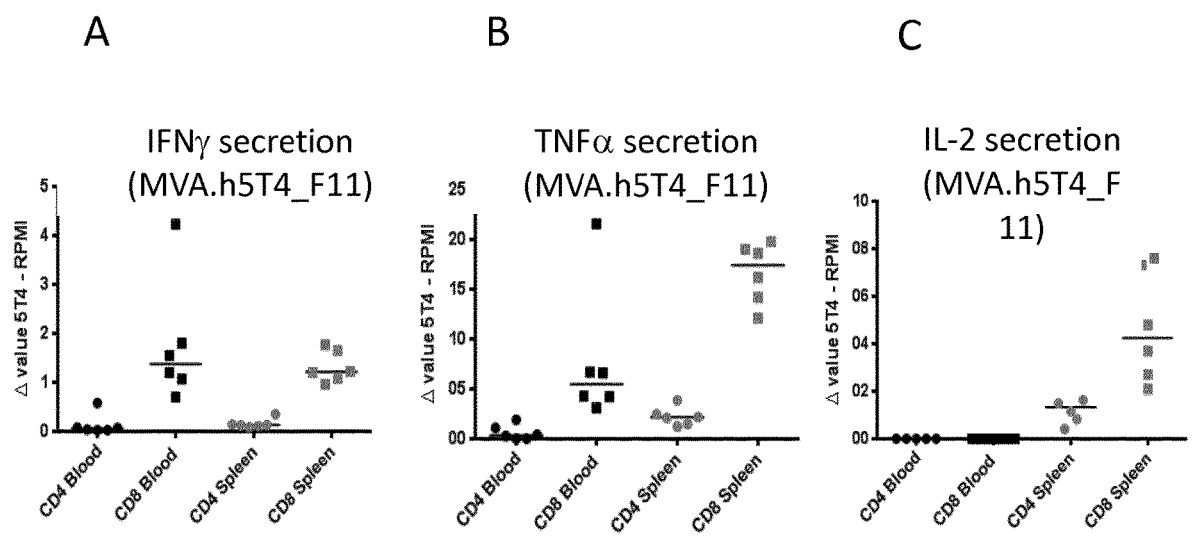
FIG. 4 illustrates the flow cytometry analysis of 5T4 specific T cells in blood and spleen from the mice primed with ChAdOx1.5T4 and boosted with MVA.5T4_F11 demonstrates generation of poly-functional CD4+ and CD8+ T cells secreting multiple cytokines. Intracellular cytokine staining (ICS) was performed on PBMCs and splenocytes isolated from mice immunised with ChAdOx1.5T4 following the MVA.5T4 boost with the antigen expression driven by F11 promoter. The graphs show percentage of CD4+ and CD8+ T cells secreting IFN-γ (A), TNF-α (B) and IL-2 (C) in response to overnight in vitro stimulation with h5T4 peptide pool. X axis: CD4+ and CD8+ T cell responses in blood and spleen. Y axis: % of 5T4 specific cytokine secreting T cells. Δ values are calculated by subtracting the background (i.e. percentage of the T cells spontaneously secreting cytokines without specific stimulation) from the percentage of the cytokine secreting T cells following exposure to the h5T4 peptide pool. Bars represent median values.

In a first aspect the present invention provides a composition for inducing a T cell mediated immune response for the treatment or prevention of prostate cancer comprising a modified Vaccinia virus Ankara (MVA) vector expressing the 5T4 antigen polypeptide under control of a poxvirus F11 promoter. MVA expressing the 5T4 antigen polypeptide expressed under the control of a poxvirus F11 promoter has not been disclosed previously and is therefore novel. Such compositions can be advantageously used to break immune tolerance to and induce T cell-mediated immune responses against the 5T4 antigen, and this can allow effective treatment or prevention of prostate cancer.

The prior art suggests a prejudice against the use of the unmodified 5T4 antigen in a vaccine for treatment or prevention of prostate cancer. Cappuccini 2017 (ibid.) confirmed that antibody responses to 5T4 can be achieved by MVA expression of unmodified 5T4 antigen as part of a homologous or heterologous prime-boost regimens. However, generation of an in vitro T cell-mediated immune response to the 5T4 antigen expressed by MVA in a heterologous prime-boost regimen required fusion of the antigen with the MHC class 2-associated invariant chain (Ii). It is an advantage of the present invention that robust cellular immune responses are induced by unmodified 5T4 antigens expressed by MVA under the control of the endogenous F11 promoter.

Prior art prime-boost using MVA-based vaccine candidates produces robust T cell immune responses against a large number of different "non-self" antigens in various indications. It is an advantage of the invention that immune tolerance is broken and a similarly robust T cell-mediated immune response is generated against a "self" antigen. This response was unexpected and provides a number of benefits including more effective treatment and a simpler development and manufacturing scheme because no antigen modification or fusions are necessary.

Preferably the MVA vector expresses the 5T4 antigen polypeptide under the control of the endogenous F11 promoter of MVA. Insertion of polynucleotides encoding antigens in the F11 locus of MVA under the control of the endogenous F11 promoter has been described previously in international publication WO 2011/128704. Such a vector expressing the 5T4 antigen polypeptide under the control of the endogenous F11 promoter has not been disclosed previously and is therefore novel. Advantageously, this conformation simplifies manufacture of the MVA vector. Additionally, Kozac-like sequences in the F11 flanking sequence are believed to aid translation initiation in eukaryotic cells and so boost expression of the 5T4 antigen by the MVA.

The present inventors provide a vaccine for treatment or prevention of prostate cancer comprising a MVA viral vector containing a nucleic acid sequence encoding the full-length, unmodified human 5T4 antigen polypeptide having the amino acid sequence of SEQ ID NO:1. The MVA construct is made such that there is no marker gene present in the recombinant virus.

The MVA vaccine construct of the present invention ((F11)5T4) was compared to MVA constructs expressing the 5T4 antigen under the control of the modified H5 early promoter ((mH5)5T4) or under the control of the p7.5 early/late promoter ((p7.5)5T4) in a mouse model to measure T cell-mediated immune responses. When administered as part of a heterologous prime-boost regimen the MVA (F11)5T4 construct induced robust 5T4-specific T-cell responses, as measured using IFNγ ELISPOT assays in peripheral blood mononuclear cells (PBMCs) and in splenocytes (FIG. 3). This response in PBMCs was more than 3-fold greater than that induced by MVA(p7.5)5T4 while no detectable response in PBMCs was induced using MVA (mH5)5T4 (FIG. 3A). The same MVA(F11)5T4 construct failed to induce the same 5T4 specific response when administered alone in a homologous prime-boost regimen. Advantageously, MVA(F11)5T4 was effective in breaking tolerance to induce a robust T cell response against 5T4 and is therefore expected to be effective in treating or preventing prostate cancer.

In certain embodiments the poxvirus F11 promoter is the endogenous MVA F11 promoter. Endogenous enhancer sequences and Kozac-like sequences in the region of the MVA F11 promoter serve to enhance transcription of the 5T4 antigen in human cells.

In a particular embodiment the 5T4 antigen polypeptide has the amino acid sequence provided in SEQ ID NO:1.

In another particular embodiment the 5T4 antigen polypeptide has the amino acid sequence encoded by the nucleic acid sequence provided in SEQ ID NO:2. The use of such a codon-optimised sequence encoding the 5T4 antigen polypeptide improves expression of the antigen polypeptide in the subject after administration of the composition.

In certain embodiments the composition further comprises an adjuvant. Inclusion of an adjuvant can improve the immune response generated on administration of the composition to a subject.

The invention also provides the use of the composition as defined above in the induction of a T cell-mediated immune response to the 5T4 antigen polypeptide. The inventors have found that administration of the composition is effective in inducing such an immune response against 5T4, a "self" antigen. The composition is preferably used to induce a $CD8^+$ T cell response.

Advantageously, the composition may be usefully administered in the treatment or prevention of prostate cancer in a subject.

In another aspect the invention provides a method of inducing a T cell-mediated immune response against the 5T4 antigen polypeptide and inducing a T cell-mediated immune response for the treatment or prevention of prostate cancer comprising the administration of a composition of the first aspect to a subject in need of such a T cell-mediated immune response.

In preferred embodiments the composition of the invention is administered in the method at a dose between $1\times10^6$ and $5\times10^8$ plaque forming units (pfu). In the most preferred embodiment the composition is administered in the method at a dose of $1\times10^7$ pfu. Such doses provide robust immune responses while minimizing unnecessary administration and wastage of the composition.

In certain embodiments the T cell-mediated immune response induced by the method comprises a $CD8^+$ T cell response. Such a cytolytic T cell response is suitable for the effective removal of cells expressing the 5T4 antigen by the subject.

In preferred embodiments the method is a prime-boost method in which the composition of the first aspect is administered to the subject to induce a primary T cell mediated immune response or to boost an existing T cell mediated immune response. In a particularly preferred embodiment the composition of the first aspect is administered as the boost to a previously administered prime vaccination. Such schedules of administration have been shown to advantageously break tolerance and allow induction of robust anti-5T4 T cell responses.

Preferred prime vaccinations of the method are provided by administration of an adenovirus expressing the 5T4 antigen polypeptide, and in the most preferred embodiments the adenovirus used is ChAdOx1.

In preferred embodiments the adenovirus expressing the 5T4 antigen polypeptide is administered in the method as a dose between $1\times10^8$ and $1\times10^{12}$ virus particles (VP), and more preferably it is between $1\times10^9$ and $1\times10^{11}$ VP. In the most preferred embodiment the adenovirus is administered in the method at a dose of $1\times10^{10}$ VP. Such doses provide robust immune responses while minimizing unnecessary administration and wastage of the composition.

In additional embodiments the methods of the invention further comprise administration of a composition of the first aspect of the invention in combination with an immune checkpoint inhibitor compound. In preferred such embodiments the immune checkpoint inhibitor compound is an anti-PD1 monoclonal antibody.

Throughout the present specification and the accompanying claims the words "comprise" and "include" and variations such as "comprises", "comprising", "includes" and "including" are to be interpreted inclusively. That is, these words are intended to convey the possible inclusion of other elements or integers not specifically recited, where the context allows.

Examples

MVA Construction

A codon optimised polynucleotide encoding the 5T4 antigen polypeptide ((NCBI Reference Sequence: NM_006670.4) was synthesised by GeneArt Gene Synthesis (Thermo Fisher Scientific). The 5T4 transgene was then cloned into a shuttle plasmid vector designed to have the upstream and downstream (flanks) of the F11L ORF as homologous sequence arms. Inserting the 5T4 transgene within these arms enabled the utilisation of the endogenous F11 promoter, which is part of the right homologous arm, while deleting the native F11L ORF. This resulted in the shuttle vector for generation of MVA.(F11)5T4 (F11 shuttle vector).

MVA.(mH5)5T4 and MVA.(p7.5)5T4 were constructed as previously described in Harrop et al (2010) and Cappuccini et al (2017) respectively.

The MVA constructs were made such that there is no marker gene is present in the recombinant virus.

5T4 Immunogenicity

Groups of 6 male C57BL/6 mice (Harlan, UK) received a prime immunization on day 0 that consisted of intramuscular (i.m.) administration of $1 \times 10^{10}$ VP ChAdOx1.5T4 (Groups 1 to 3) or $1 \times 10^7$ pfu MVA.(F11)5T4 (Group 4).

The same animals received a boost immunization on day 21 consisting of i.m administration of $1 \times 10^7$ pfu MVA.(p7.5) 5T4 (Group 1), $1 \times 10^7$ pfu MVA.(F11)5T4 (Group 2), $1 \times 10^7$ pfu MVA.(mH5)5T4 (Group 3) or $1 \times 10^7$ pfu MVA.(F11)5T4 (Group 4).

Blood and spleen from each mouse were collected 3 weeks after the boost (day 42) and PBMCs and splenocytes were tested for the presence of 5T4 specific T cells by IFNg ELISPOT. Results of ELISPOT analysis are provided in FIG. 3.

Flow cytometry analysis of 5T4 specific T cells was also performed on PBMCs and splenocytes from the mice primed with ChAdOx1.5T4 and boosted with MVA. (F11)5T4. Results of flow cytometry analysis are provided in FIG. 4.

All animal procedures were performed in accordance with the terms of the UK Animals (Scientific Procedures) Act (ASPA) for the project license 30/2947 and were approved by the University of Oxford Animal Care and Ethical Review Committee. All mice were housed for at least 7 days for settlement prior to any procedure in the University animal facility, Oxford, UK under Specific Pathogen Free (SPF) conditions.

MVA-(F11)5T4 Safety and Immunogenicity in Human Subjects

MVA-(F11)5T4 has been administered to human subjects in clinical trials to treat late stage metastatic prostate cancer.

These prostate cancer patients received a priming immunization on week 0 that consisted of intramuscular (i.m.) administration of a simian adenoviral vector ChAdOx1 encoding 5T4 at a dose of $2 \times 10^{10}$ vp and a booster intramuscular dose of MVA-(F11)5T4 at week 4 together with an intravenous dose of the checkpoint inhibitor anti-PD1. The same patients are receiving a second round of immunizations at 12 and 16 weeks and further standard i.v. doses of anti-PD1 at 8 and 12 weeks. Blood samples are collected at weeks 0, 2, 5, 9, 13, 17, 24 and 36 to measure immune responses, and any adverse events (AEs) are being documented and investigated.

11 patients have been administered the MVA-(F11)5T4, and the safety profile has been very good. 50% of patients reported pain or tenderness at the injection site the day following vaccination. There have been three (3) serious adverse events (SAEs), but investigation has concluded that none of them were due to MVA-(F11)5T4.

What is claimed is:

1. A composition for inducing a T cell mediated immune response for the treatment or prevention of prostate cancer comprising a modified Vaccinia virus Ankara (MVA) vector expressing the 5T4 antigen polypeptide under control of a poxvirus F11 promoter, wherein the vector expresses a polypeptide encoded by a polynucleotide having the nucleic acid sequence of SEQ ID NO: 2.

2. The composition according to claim 1, wherein the poxvirus F11 promoter is the endogenous MVA F11 promoter.

3. The composition according to claim 1, wherein the vector expresses a polypeptide having the amino acid sequence of SEQ ID NO: 1.

4. The composition according to claim 1 further comprising an adjuvant.

* * * * *

SEQUENCE LISTING

```
<160> NUMBER OF SEQ ID NOS: 2

<210> SEQ ID NO 1
<211> LENGTH: 420
<212> TYPE: PRT
<213> ORGANISM: Homo sapiens
<220> FEATURE:
<223> OTHER INFORMATION: >1

<400> SEQUENCE: 1

Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
                20                  25                  30

Ser Pro Thr Ser Ser Ala Ser Ser Phe Ser Ser Ser Ala Pro Phe Leu
            35                  40                  45

Ala Ser Ala Val Ser Ala Gln Pro Pro Leu Pro Asp Gln Cys Pro Ala
        50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Ala Tyr Val Arg Asn Leu
                85                  90                  95

Phe Leu Thr Gly Asn Gln Leu Ala Val Leu Pro Ala Gly Ala Phe Ala
            100                 105                 110

Arg Arg Pro Pro Leu Ala Glu Leu Ala Ala Leu Asn Leu Ser Gly Ser
        115                 120                 125

Arg Leu Asp Glu Val Arg Ala Gly Ala Phe Glu His Leu Pro Ser Leu
    130                 135                 140

Arg Gln Leu Asp Leu Ser His Asn Pro Leu Ala Asp Leu Ser Pro Phe
145                 150                 155                 160
```

-continued

Ala Phe Ser Gly Ser Asn Ala Ser Val Ser Ala Pro Ser Pro Leu Val
            165                 170                 175

Glu Leu Ile Leu Asn His Ile Val Pro Pro Glu Asp Glu Arg Gln Asn
        180                 185                 190

Arg Ser Phe Glu Gly Met Val Val Ala Ala Leu Leu Ala Gly Arg Ala
        195                 200                 205

Leu Gln Gly Leu Arg Arg Leu Glu Leu Ala Ser Asn His Phe Leu Tyr
    210                 215                 220

Leu Pro Arg Asp Val Leu Ala Gln Leu Pro Ser Leu Arg His Leu Asp
225                 230                 235                 240

Leu Ser Asn Asn Ser Leu Val Ser Leu Thr Tyr Val Ser Phe Arg Asn
                245                 250                 255

Leu Thr His Leu Glu Ser Leu His Leu Glu Asp Asn Ala Leu Lys Val
            260                 265                 270

Leu His Asn Gly Thr Leu Ala Glu Leu Gln Gly Leu Pro His Ile Arg
        275                 280                 285

Val Phe Leu Asp Asn Asn Pro Trp Val Cys Asp Cys His Met Ala Asp
    290                 295                 300

Met Val Thr Trp Leu Lys Glu Thr Glu Val Val Gln Gly Lys Asp Arg
305                 310                 315                 320

Leu Thr Cys Ala Tyr Pro Glu Lys Met Arg Asn Arg Val Leu Leu Glu
                325                 330                 335

Leu Asn Ser Ala Asp Leu Asp Cys Asp Pro Ile Leu Pro Pro Ser Leu
            340                 345                 350

Gln Thr Ser Tyr Val Phe Leu Gly Ile Val Leu Ala Leu Ile Gly Ala
        355                 360                 365

Ile Phe Leu Leu Val Leu Tyr Leu Asn Arg Lys Gly Ile Lys Lys Trp
    370                 375                 380

Met His Asn Ile Arg Asp Ala Cys Arg Asp His Met Glu Gly Tyr His
385                 390                 395                 400

Tyr Arg Tyr Glu Ile Asn Ala Asp Pro Arg Leu Thr Asn Leu Ser Ser
                405                 410                 415

Asn Ser Asp Val
            420

<210> SEQ ID NO 2
<211> LENGTH: 1266
<212> TYPE: DNA
<213> ORGANISM: Homo sapiens
<220> FEATURE:
<223> OTHER INFORMATION: >2

<400> SEQUENCE: 2
atgcctggcg gctgtagcag aggacctgct gctggcgacg gtagactgag actggctaga      60
ctggcactgg tgctgcttgg ctgggtgtcc tctagcagcc ctacaagcag cgccagctcc     120
tttagcagca gcgcccccttt tctggcctct gccgtttctg ctcaacctcc tctgcctgat     180
cagtgccctg ctctgtgcga gtgttctgag ccgccagaa cagtgaagtg cgtgaacaga     240
aacctgaccg aggtgcccac agacctgcct gcctacgtgc ggaatctgtt cctgaccgga     300
aatcagctgg ccgtgcttcc tgctggcgcc tttgctagaa ggcctccact ggctgaactg     360
gccgctctga atctgagcgg cagcagactg gatgaagttc gcgctggcgc tttcgagcat     420
ctgccttctc tgagacagct ggacctgagc cacaatcctc tggccgatct gagcccttt     480 gccttcagcg gaagcaacgc ctctgtgtct gctccatctc cactggtcga gctgatcctg     540

-continued

```
aaccacatcg tgcctccaga ggacgagcgg cagaacagat cctttgaagg catggtggtg    600
gctgccctgc ttgctggtag agcactgcaa ggactgcgga gactggaact ggccagcaac    660
cacttcctgt acctgcctag agatgtgctg gcccagctgc ctagcctgag gcatctggat    720
ctgtccaaca acagcctggt gtccctgacc tacgtgtcct tccggaatct gacccacctg    780
gaaagcctgc acctggaaga taacgccctg aaggtgctgc acaatggcac cctggcagaa    840
ctgcagggcc tgcctcacat cagagtgttt ctggacaaca acccctgggt ctgcgactgc    900
cacatggccg atatggtcac ctggctgaaa gaaaccgagg tggtgcaggg caaagaccgg    960
ctgacatgtg cttaccccga gaagatgcgg aaccgggtgc tgctggaact gaacagcgcc    1020
gacctggact gcgatcctat tctgccacct agcctgcaga ccagctacgt gttcctggga    1080
atcgtgctgg ctctgatcgg cgccatcttt ctgctggtgc tgtacctgaa ccggaagggc    1140
atcaagaaat ggatgcacaa catccgggac gcctgccggg atcacatgga aggctaccac    1200
tacagatacg agatcaacgc cgatcctcgg ctgaccaacc tgagcagcaa tagcgacgtg    1260
tgatga                                                               1266
```